US010065877B2

(12) United States Patent
Hori et al.

(10) Patent No.: US 10,065,877 B2
(45) Date of Patent: Sep. 4, 2018

(54) **MICROORGANISM BELONGING TO *YARROWIA* GENUS, AND OIL DECOMPOSITION AGENT AND OIL DECOMPOSITION/REMOVAL METHOD USING SAME**

(71) Applicant: National University Corporation Nagoya University, Nagoya-shi (JP)

(72) Inventors: Katsutoshi Hori, Nagoya (JP); Masatake Fujioka, Nagoya (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 201 days.

(21) Appl. No.: 14/372,831

(22) PCT Filed: Jan. 16, 2013

(86) PCT No.: PCT/JP2013/050649
§ 371 (c)(1),
(2) Date: Jul. 17, 2014

(87) PCT Pub. No.: WO2013/108775
PCT Pub. Date: Jul. 25, 2013

(65) Prior Publication Data
US 2015/0024470 A1    Jan. 22, 2015

(30) Foreign Application Priority Data

Jan. 19, 2012 (JP) ................. 2012-009451

(51) Int. Cl.
| | | |
|---|---|---|
| *C12N 1/16* | (2006.01) | |
| *C12P 7/20* | (2006.01) | |
| *C12P 7/40* | (2006.01) | |
| *C12R 1/00* | (2006.01) | |
| *C02F 3/34* | (2006.01) | |
| *C02F 101/32* | (2006.01) | |
| *C02F 103/32* | (2006.01) | |

(52) U.S. Cl.
CPC .............. *C02F 3/343* (2013.01); *C02F 3/341* (2013.01); *C12N 1/16* (2013.01); *C12P 7/20* (2013.01); *C12P 7/40* (2013.01); *C12R 1/00* (2013.01); *C02F 3/347* (2013.01); *C02F 2101/32* (2013.01); *C02F 2103/32* (2013.01); *C02F 2103/322* (2013.01); *C02F 2307/08* (2013.01)

(58) Field of Classification Search
None
See application file for complete search history.

(56) References Cited

U.S. PATENT DOCUMENTS

2006/0094092 A1\* 5/2006 Damude ................ A23D 9/00
435/134

FOREIGN PATENT DOCUMENTS

| JP | 2561441 B2 | 12/1996 |
|---|---|---|
| JP | 2006-042774 A | 2/2006 |
| JP | 2010-227849 A | 10/2010 |
| JP | 2010-227858 A | 10/2010 |
| JP | 2011-160713 A | 8/2011 |

OTHER PUBLICATIONS

Papanikolaou et al. (European Journal of Lipid Science and Technology, vol. 105 pp. 651-655; 2003 (of record).\*
Matsuoka et al. (Journal of Bioscience and Bioengineering, vol. 107, No. 4, pp. 401-408; 2009 (of record).\*
Matsuoka et al. (Journal of Bioscience and Bioengineering, vol. 107, No. 4, pp. 401-408; 2009) (of record).\*
H. Matsuoka et al., "Symbiotic effects of a lipase-secreting bacterium, *Burkholderia arboris* SL1B1, and a glycerol-assimilating yeast, *Candida cylindracea* SL1B2, on triacylglycerol degradation", Journal of Bioscience and Bioengineering, vol. 107, No. 4, Apr. 1, 2009, pp. 401-408.
M.A.Z. Coelho et al., "*Yarrowia lipolytica*: an industrial workhorse", Current Research, Technology and Education Topics in Applied Microbiology and Microbial Biotechnology, Jan. 1, 2010, pp. 930-944.
Huiting Song et al., "Construction of a whole-cell catalyst displaying a fungal lipase for effective treatment of oily wastewaters", Journal of Molecular Catalysis. B: Enzymatic, vol. 71, No. 3, Apr. 18, 2011, pp. 166-170.
Seraphim Papanikolaou et al., "Selective uptake of fatty acids by the yeast *Yarrowia lipolytica*", European Journal of Lipid Science and Technology., vol. 105, No. 11, Nov. 1, 2003, pp. 651-655.
B H. Nga et al., "Genetic Analysis of Lipase Low-producing Mutants of *Yarrowia lipolytica*", Journal of General Microbiology, vol. 135, No. 9, Jan. 1, 1989, pp. 2439-2443.
L. Wu et al., "Biodegradation of oil wastewater by free and immobilized *Yarrowia lipolytica* W29", Journal of Environmental Sciences, vol. 21, No. 2, Jan. 1, 2009, pp. 237-242.
Supplementary European Search Report dated Nov. 9, 2015, issued for the European patent application No. 13738396.4.
Wu Lan et al., "Use of Yarrowia Lipolytica for the treatment of Oil/Grease Wastewater," Research of Environmental Science, vol. 19, No. 5, 2006, pp. 122-125 and English abstract thereof.
Office Action dated Jun. 3, 2015, issued for the corresponding Chinese patent application No. 201380005842.X.
H. Song et al., "Construction of a whole-cell catalyst displaying a fungal lipase for effective treatment of oily wastewaters," J. Mol. Catal. B. Enzym. vol. 71 No. 3-4, 2011, pp. 166-170.

(Continued)

*Primary Examiner* — Soren Harward
*Assistant Examiner* — Paul D. Pyla
(74) *Attorney, Agent, or Firm* — Locke Lord LLP

(57) ABSTRACT

The present invention addresses the problem of providing a new microorganism that is useful for efficiently decomposing oils and fats, and a use for said microorganism. According to screening results, a new *Yarrowia lipolytica* having a high capacity to assimilate free fatty acids was successfully obtained. Efficient decomposition of oils and fats is achieved by causing the *Yarrowia lipolytica* to act under conditions in which fatty acids that are hydrolysis products of oils or fats are present, or under conditions in which oils or fats are decomposed into fatty acids and glycerol.

8 Claims, 9 Drawing Sheets

(56) References Cited

OTHER PUBLICATIONS

A. Domínguez et al., "Biodegradation and utilization of waste cooking oil by Yarrowia lipolytica CECT 1240," Eur. J. Lipid. Sci. Technol. vol. 112, No. 11, 2010, pp. 1200-1208.
International Search Report dated Mar. 5, 2013, issued for PCT/JP2013/050649.
Official Communication Pursuant to Article 94(3) EPC for European Patent Office Application 13 738 396.4, dated Feb. 15, 2018.
Pignede G et al: Characterization of an Extracellular Lipase Encoded by LIP2 in Yarrowia lipolytica, Journal of Bacteriology, American Society for Microbiology, US,vol. 182, No. 10, May 1, 2000, pp. 282-2810, ISSN: 0021-9193, DOI: 10.1128/JB.182.10.2802-2810.2000.

\* cited by examiner

[Fig. 1]
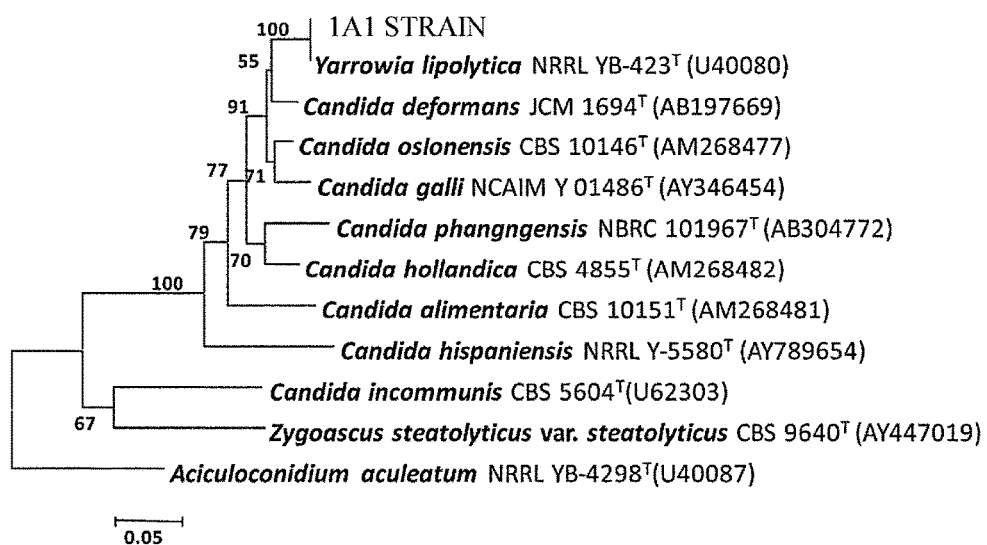

[Fig. 2]
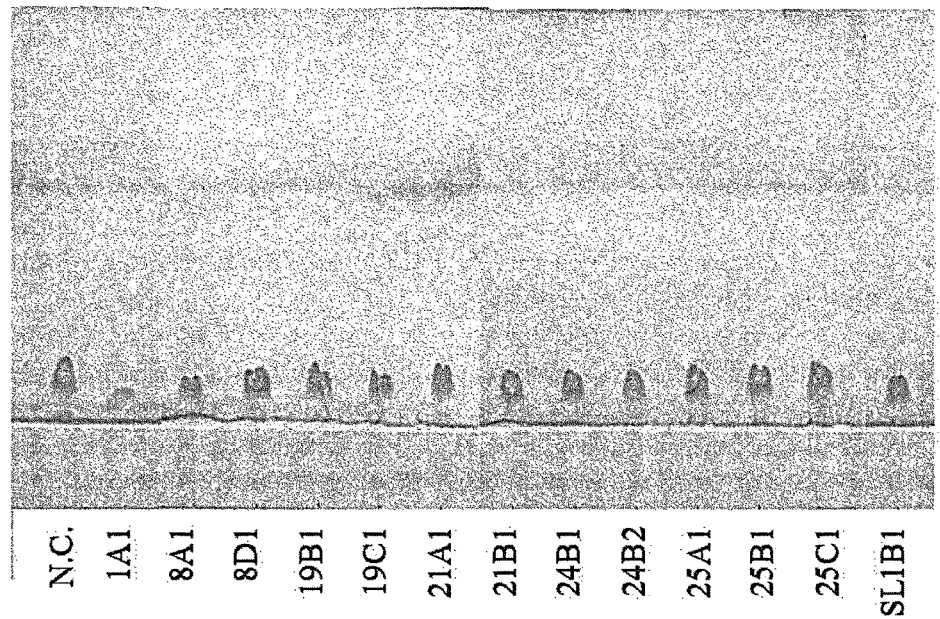

[Fig. 3]
CARBON SOURCE : 1% CANOLA OIL
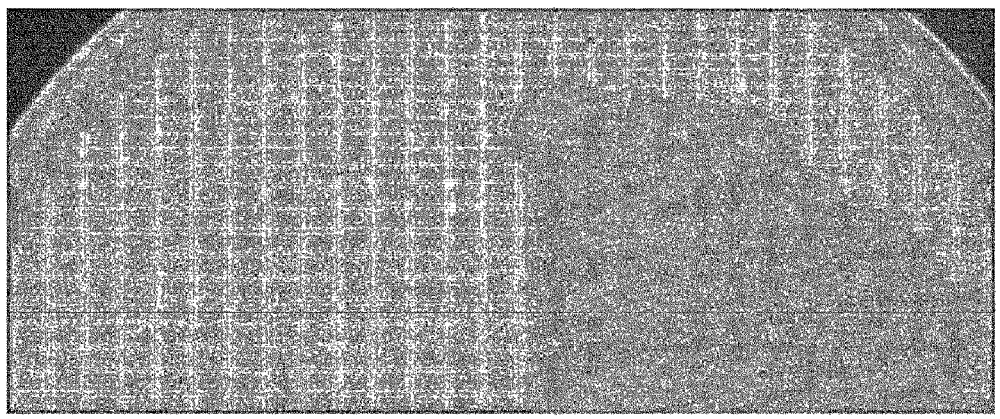
1A1　　　　　　　　SL1B1
CARBON SOURCE : 1% OLEIC ACID
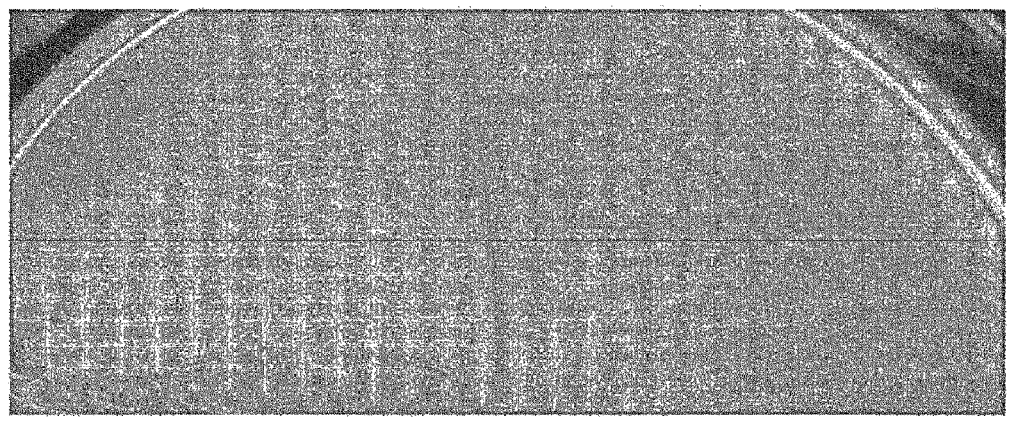
1A1　　　　　　　　SL1B1

[Fig. 4]
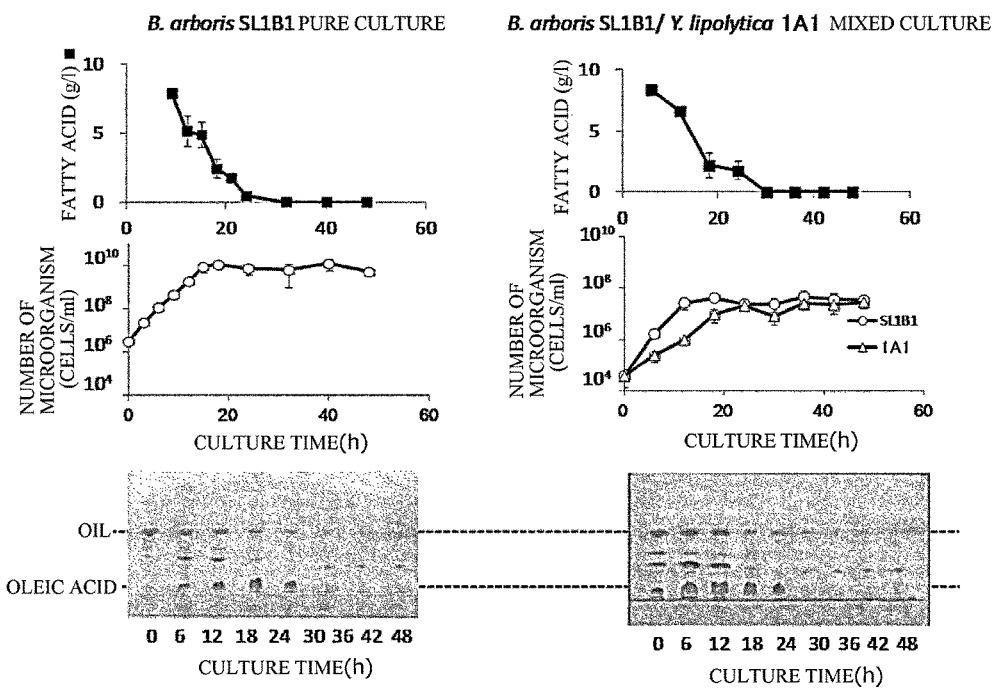

[Fig.5]
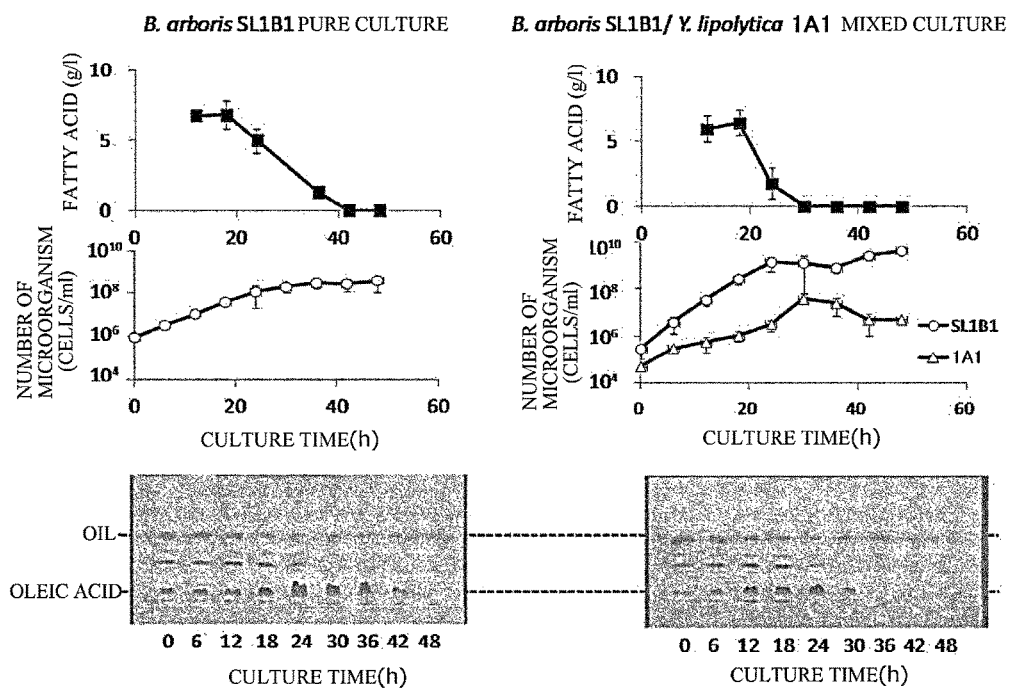

[Fig. 6]
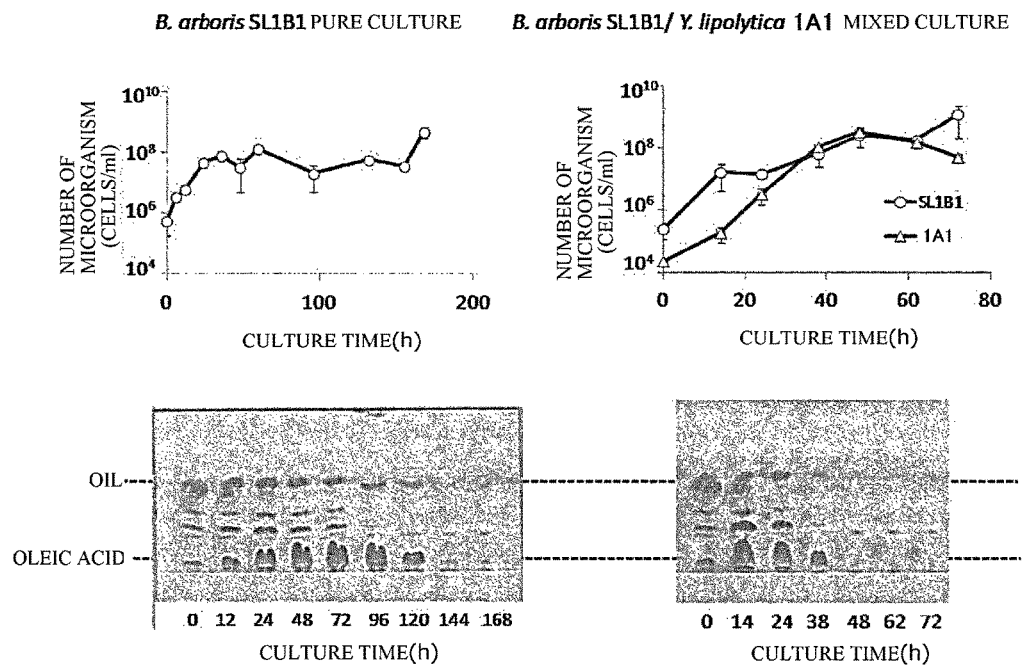

[Fig. 7]
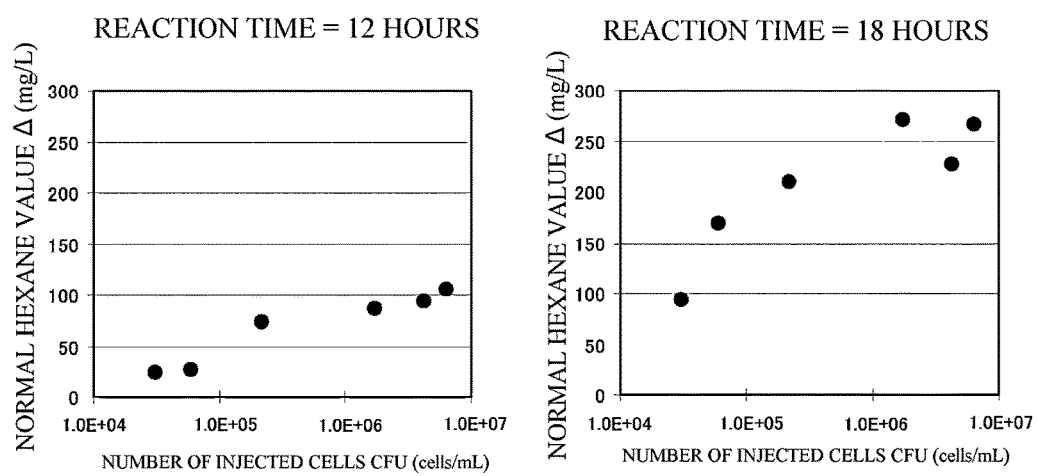

[Fig. 8]
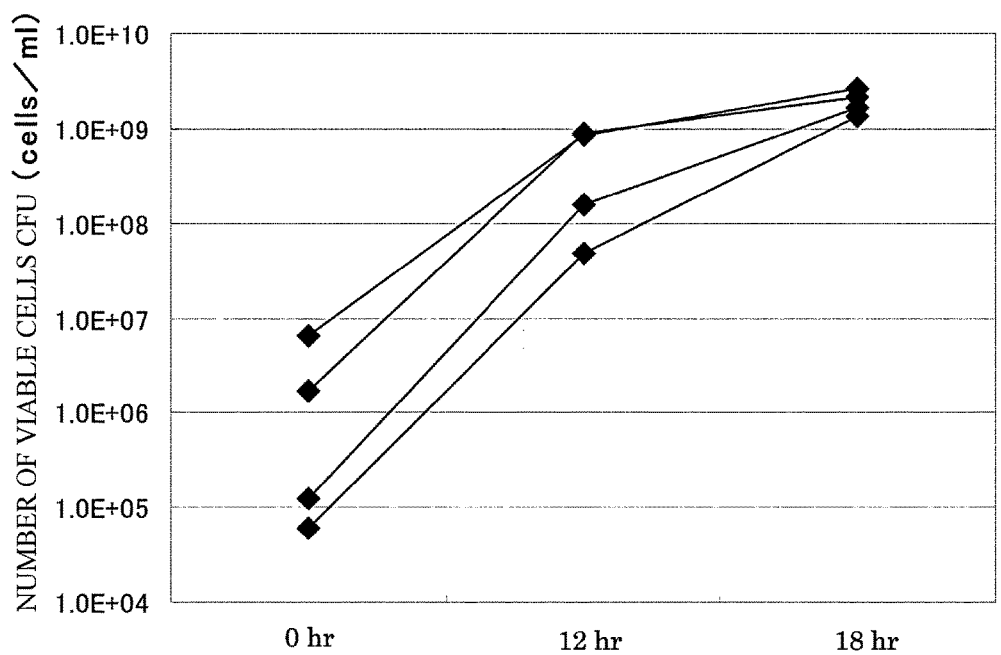

[Fig. 9]

(COMPARATIVE EXAMPLE 1) WITHOUT MICROORGANISM FORMULATION

| DAYS AFTER INITIATION OF INJECTION | 0 | 2 | 7 | 14 | 21 | 28 |
|---|---|---|---|---|---|---|
| NORMAL HEXANE VALUE (mg/L) | 4800 | 4500 | 6800 | 3400 | 3900 | 4700 |

(COMPARATIVE EXAMPLE 2) *B. arboris* SL1B1 + *Candida cylindracea* SL1B2

| DAYS AFTER INITIATION OF INJECTION | 0 | 2 | 7 | 14 | 21 | 28 |
|---|---|---|---|---|---|---|
| NORMAL HEXANE VALUE (mg/L) | 5200 | 1500 | 850 | 250 | 110 | 120 |

(EXAMPLE) *B. arboris* SL1B1 + *Candida cylindracea* SL1B2 + *Y. lipolytica* 1A1

| DAYS AFTER INITIATION OF INJECTION | 0 | 2 | 7 | 14 | 21 | 28 |
|---|---|---|---|---|---|---|
| NORMAL HEXANE VALUE (mg/L) | 4900 | 970 | 280 | 54 | 22 | 27 |

# MICROORGANISM BELONGING TO *YARROWIA* GENUS, AND OIL DECOMPOSITION AGENT AND OIL DECOMPOSITION/REMOVAL METHOD USING SAME

TECHNICAL FIELD

The present invention relates to decomposition of oils and fats. Specifically, the present invention relates to a novel microorganism belonging to the genus *Yarrowia*, which is useful for the decomposition of oils and fats in waste water, a grease trap or the like, oil and fat decomposing agent and a method for decomposing and removing oils and fats using the microorganism, and the like. The present application claims a priority based on Japanese Patent Application No. 2012-009451 filed on Jan. 19, 2012, and the whole content of the patent application is herein incorporated by reference.

BACKGROUND ART

Decomposition of oils and fats by a microorganism is utilized for a waste water treatment and the like. Especially, considering that a grease trap that is a treatment device configured to remove an oil component included in kitchen waste water in the restaurant industry by solid-liquid separation is a source of bad odor and pest insects, and the toil and cost required for the collection and transportation of the separated oil, and maintenance such as cleaning, and the like, establishment of an innovative technology that eliminates an oil in a grease trap has been desired by the industries, mainly by the restaurant industry, and thus application of an oil and fat decomposition technology by microorganisms has been tried. However, since kitchen waste water in the restaurant industry contains oils and fats generally at 1 g/L or more, or at a higher concentration of as high as 10 g/L or more, and waste water in many grease traps has an extremely short retention time of about 10 minutes, it is difficult to treat an oil in only a grease trap, and an oil and fat decomposing agent that is sufficient to practical use is still desired.

Under such circumstance, one of the present inventors reported a novel microorganism (*Burkholderia arboris*) that secretes lipase, triacylglycerol hydrolase, as a microorganism that effectively treats oils and fats-containing waste water (Patent Literature 1). On the other hand, the inventor also reported a means for promoting the decomposition of oils and fats by using a microorganism having excellent glycerol assimilation property in combination (Patent Literature 2).

PRIOR ART DOCUMENT

Patent Document

Patent Literature 1: JP 2010-227858 A
Patent Literature 2: JP No. 2010-227849 A
Patent Literature 3: JP 2011-160713 A
Patent Literature 4: JP 2561441 B1
Patent Literature 5: JP 2006-42774 A

Non-Patent Document

Non-patent Literature 1: J. Mol. Catal. B. Enzym. Vol. 71 No. 3-4, p. 166-170, 2011
Non-patent Literature 2: Eur. J. Lipid. Sci. Technol. Vol. 112, No. 11, p. 1200-1208, 2010

SUMMARY OF THE INVENTION

Problem to be Solved by the Invention

The hydrolysis reaction of triacylglycerol, a main component of oils and fats, is a reversible reaction, and when the decomposition of oils and fats proceeds, fatty acids and glycerol as the hydrolysis products of the triacylglycerol accumulate, and the hydrolysis velocity decreases. In the technology shown in the above-mentioned Patent Literature 2, the decomposition of the oils and fats is promoted by removing glycerol, which is one of the hydrolysis products, by a microorganism having an excellent glycerol assimilation property. However, as the hydrolysis products, the fatty acids are overwhelmingly more than the glycerol. The released fatty acids (free fatty acids) themselves are also oil components, and thus should be removed together with triacylglycerol. Especially in the case when a microorganism having an extremely high triacylglycerol hydrolysis ability such as the microorganism reported in Patent Literature 1 is used, the consumption of the fatty acids by the microorganism cannot catch up with the generation, and thus large amounts of free fatty acids accumulate in a treatment tank, and lowering of the oil and fat decomposition efficiency itself is also caused.

Accordingly, the object of the present invention is to provide a novel microorganism that is useful in effective decomposition and removal of oils and fats, and use thereof, so as to solve the above-mentioned problem.

Means for Solving Problem

Under the above-mentioned object, the present inventors envisaged a combination use with a microorganism having an excellent triacylglycerol hydrolysis ability and other triacylglycerol hydrolysis agents (a lipase formulation and the like), and attempted to obtain a microorganism having an excellent fatty acid assimilation ability. Specifically, microorganisms were screened from grease in a grease trap tank, and environment samples such as soils, sludge and lake water, by using fatty acid assimilation abilities as an indicator, and the properties were investigated and the bacterial species were identified. As a result, plural strains of *Yarrowia lipolytica* were identified as microorganisms having an extremely high ability of fatty acid assimilation. In general, *Yarrowia lipolytica* is known as a lipase-secreting microorganism, and the application thereof to the decomposition of oils and fats has been conventionally attempted (for example, Patent Literatures 3 to 5 and Non-patent Literatures 1 and 2, and the like). Surprisingly, all of the *Yarrowia lipolytica* strains that were successfully identified show a high fatty acid assimilation ability, but do not show an oil and fat decomposition ability (i.e., do not secrete lipase). There has been no previous report on any *Yarrowia lipolytica* that shows such property.

The inventors have further studied, and found that the *Yarrowia lipolytica* strains that were successfully identified can grow symbiotically with *Burkholderia arboris*, which has a high ability of triacylglycerol hydrolysis, and promote the decomposition of oils and fats by combination use with the *Burkholderia arboris*. It is particularly worth noting that, when these two kinds of microorganisms were used in combination, drastic improvement of the efficiency of oil and fat decomposition and removal was able to be achieved under a low temperature environment in which oils and fats are difficult to be decomposed. Furthermore, the oils and fats were also able to be efficiently decomposed and removed under a condition in which oils and fats are present at high concentrations. Considering an actual use environment for which harsh treatment conditions are expected, these effects can be considered to be extremely advantageous in practical use. In fact, the effectiveness for actual waste water was also verified, and the usefulness and practicality of the novel microorganisms (*Yarrowia lipolytica*) that had been successfully obtained were confirmed (see Examples mentioned below). On the other hand, it was clarified also in a verification experiment using an existing grease trap that combination use of the microorganism that had been successfully obtained lead to drastic improvement of the efficiency of decomposition and removal of oils and fats (see Examples mentioned below).

The present invention shown below is based on mainly the above-mentioned achievement.

[1] A method for decomposing and removing oils and fats, including causing *Yarrowia lipolytica* that assimilates free fatty acids to act under first condition in which fatty acids that are hydrolyzed products of triacylglycerol are present, or under second condition in which triacylglycerol is hydrolyzed into fatty acids and glycerol.

[2] The method according to [1], wherein the *Yarrowia lipolytica* is *Yarrowia lipolytica* that does not secrete a lipase.

[3] The method according to [1] or [2], wherein the *Yarrowia lipolytica* is a strain that can grow symbiotically with *Burkholderia arboris*.

[4] The method according to [1], wherein the *Yarrowia lipolytica* is a strain specified by Accession No. NITE BP-1167.

[5] The method according to any one of [1] to [4], wherein the second condition is a condition under which lipase is present.

[6] The method according to any one of [1] to [4], wherein the second condition is a condition under which a microorganism capable of secreting a lipase is present.

[7] The method according to [6], wherein the microorganism is *Burkholderia arboris*.

[8] The method according to [7], wherein the *Burkholderia arboris* is a strain specified by Accession No. NITE P-724.

[9] The method according to any one of [1] to [8], wherein a microorganism that assimilates glycerol is used in combination.

[10] The method according to [9], wherein the microorganism that assimilates glycerol is *Candida cylindracea*.

[11] The method according to [10], wherein the *Candida cylindracea* is a strain specified by Accession No. NITE P-714.

[12] The method according to any one of [1] to [11], wherein the oils and fats are oils and fats in waste water or a grease trap.

[13] A method for treating waste water, including decomposing and removing oils and fats in waste water by the method according to any one of [1] to [11].

[14] A method for clarifying a grease trap, including decomposing and removing oils and fats in a grease trap by the method according to any one of [1] to [11].

[15] *Yarrowia lipolytica* having the following properties:
(1) the *Yarrowia lipolytica* assimilates free fatty acids;
(2) the *Yarrowia lipolytica* does not secrete a lipase; and
(3) the *Yarrowia lipolytica* can grow symbiotically with *Burkholderia arboris*.

[16] The *Yarrowia lipolytica* according to [15], which is a strain specified by Accession No. NITE BP-1167.

[17] An oil and fat decomposing agent containing the *Yarrowia lipolytica* according to [15] or [16] as an active ingredient.

[18] An oil and fat decomposing agent including the *Yarrowia lipolytica* according to [15] or [16] and a component that hydrolyzes triacylglycerol into fatty acids and glycerol in combination.

[19] The oil and fat decomposing agent according to [18], which contains the *Yarrowia lipolytica* and the component.

[20] The oil and fat decomposing agent according to [18], which is a kit including a first element containing the *Yarrowia lipolytica*, and a second element containing the component.

[21] The oil and fat decomposing agent according to [18], which contains the *Yarrowia lipolytica*, and is used in combination with a component that hydrolyzes triacylglycerol into fatty acids and glycerol.

BRIEF DESCRIPTION OF DRAWING

FIG. 1 shows the result of a phylogenetic analysis of *Yarrowia lipolytica* (*Y. lipolytica*) 1A1 strain.

FIG. 2 shows the comparison of the oleic acid decomposition abilities of the screened 12 strains. The residual oleic acid in the culture medium was analyzed by TLC.

FIG. 3 shows the growth potential of *Y. lipolytica* 1A1 strain. The growth was observed on agar culture media to which 10 g/L (1%) of canola oil (upper) and 10 g/L (1%) of oleic acid (lower) were respectively added as carbon sources. As a comparative bacterium, *Burkholderia arboris* (*B. arboris*) SL1B1 strain was used.

FIG. 4 shows oil and fat decomposition behavior at 28° C. (the amount of the oils and fats was 10 g/L). The case when *B. arboris* SL1B1 strain was subjected to pure culturing (left) and the case when *B. arboris* SL1B1 strain and *Y. lipolytica* 1A1 strain were subjected to mix culturing (right) were compared.

FIG. 5 shows oil and oil and fat decomposition behavior at 22° C. (the amount of the oils and fats was 10 g/L). The case when *B. arboris* SL1B1 strain was subjected to pure culturing (left) and the case when *B. arboris* SL1B1 strain and *Y. lipolytica* 1A1 strain were subjected to mix culturing (right) were compared.

FIG. 6 shows oil and fat decomposition behavior at 22° C. (the amount of the oils and fats was 30 g/L). The case when *B. arboris* SL1B1 strain was subjected to pure culturing (left) and the case when *B. arboris* SL1B1 strain and *Y. lipolytica* 1A1 strain were subjected to mix culturing (right) were compared.

FIG. 7 shows decreased amounts of normal hexane values in an oil and fat decomposition experiment in actual waste water by a mixed microorganism formulation. A microorganism formulation in which *B. arboris* SL1B1 strain and *Y. lipolytica* 1A1 strain were mixed was injected into actual waste water and reacted. The decreased amount of the normal hexane value was measured at after 12 hours (left) and after 18 hours (right).

FIG. 8 shows the change in the number of viable cells at after 12 hours and after 18 hours for every number of the injected viable cells. A microorganism formulation in which *B. arboris* SL1B1 strain and *Y. lipolytica* 1A1 strain were mixed was injected into actual waste water and reacted. The numbers of viable cells at after 12 hours and after 18 hours were compared.

FIG. 9 shows a result of a verification test in a grease trap. A mixed microorganism formulation of three kinds: *B. arboris* SL1B1 strain, *Candida cylindracea* SL1B2 and *Y. lipolytica* 1A1 strain was injected into a grease trap, and the normal hexane values were measured over time. For comparison, an experimental section without a microorganism formulation (Comparative Example 1) and an experimental section in which a mixed microorganism formulation of two kinds *B. arboris* SL1B1 and *Candida cylindracea* SL1B2 strain was injected (Comparative Example 2) were provided.

DESCRIPTION OF EMBODIMENT

1. Method for Decomposing and Removing Oils and Fats

The first aspect of the present invention relates to a method for decomposing and removing oils and fats. The method for decomposing and removing oils and fats according to the present invention is utilized in the treatment of oil and fat-containing waste water, the clarification of a grease trap, and the like. Specifically, the present invention can be applied to the treatment of waste water containing oils and fats such as waste water from restaurants, hospitals, hotels and the like, household waste water, industrial waste water and the like discharged from food processing factories and grease processing factories and the like, or the decomposition and removal of oils and fats that accumulate in a grease trap installed in a kitchen or the like. The "grease trap" refers to an apparatus for separating and collecting oils and fats in waste water, and is typically constituted by three tanks. The first tank includes a basket, and captures food material pieces, uneaten foods and the like. In the second tank, the grease and water are separated. The waste water separated from the grease is fed to the third tank, and sedimentable garbage and the like are removed. Installation of a grease trap is required for professional-use kitchens in restaurants, hospitals, hotels and the like.

Examples of the oils and fats to be treated can include vegetable oils (cottonseed oil, rapeseed oil, soybean oil, corn oil, olive oil, safflower oil, rice oil, sesame oil, palm oil, coconut oil, peanut oil and the like), animal greases (lard, beef fat, milk fat and the like) and fish oils. Processed products of these oils and fats (margarine, shortening, butter and the like) can also be subjects to be treated.

The important feature of the method for decomposing and removing oils and fats of the present invention is that *Yarrowia lipolytica* that assimilates free fatty acids is caused to act under a condition in which fatty acids that are hydrolyzed products of triacylglycerol are present (hereinafter referred to as "first condition" in the present invention), or under a condition in which triacylglycerol is hydrolyzed into fatty acids and glycerol (hereinafter referred to as "second condition" in the present invention). The "caused to act" as used herein refers to formation of a state that allows contact with free fatty acids that are hydrolyzed products of oils and fats. Specifically, a formulation containing *Yarrowia lipolytica* that assimilates free fatty acids, or the like is put or added, or a support on which the *Yarrowia lipolytica* is immobilized or the like is placed in a waste water path, a waste water storage tank, a grease trap or the like. It is also possible to dispose another dedicated decomposition treatment tank outside of the grease trap.

In the present invention, by using *Yarrowia lipolytica* having an excellent ability to assimilate free fatty acids, free fatty acids generated by the hydrolysis of triacylglycerol are removed. Alternatively, the accumulation of the free fatty acids is prevented, whereby the hydrolysis of the triacylglycerol is promoted. In the case when the above-mentioned first condition is adopted, typically, the triacylglycerol is hydrolyzed in advance, and the present invention is applied. For the hydrolysis of the triacylglycerol, lipase or a microorganism capable of secreting a lipase (see the following explanation) can be utilized. On the other hand, in the case when the second condition is adopted, it is generally premised that a state under which lipase or a microorganism capable of secreting a lipase is present is formed.

In the case when either of the conditions is adopted, various lipases can be used, and for example, it is preferable to utilize commercially available lipase formulations. Examples of the lipase formulations can include lipase A10FG (manufactured by Yakult Pharmaceutical Industry Co., Ltd.), lipase AL, lipase OF and lipase MY (these are manufactured by Meito Sangyo Co., Ltd.), Lipolase, Lipex, Resinase, Lipozyme, Patalase, Lipopan and Lecithase (these are manufactured by Novozymes Japan Ltd.), lipase AS "Amano", lipase AYS "Amano", lipase PS "Amano", lipase AK "Amano", lipase PS "Amano", lipase A "Amano", lipase AY "Amano", lipase G "Amano", lipase R "Amano", lipase DF "Amano" and lipase MER "Amano" (these are manufactured by Amano Enzyme, Inc.). On the other hand, as the microorganism capable of secreting a lipase, the genus *Bacillus*, the genus *Burkholderia*, the genus *Acinetobacter*, the genus *Pseudomonas*, the genus *Alcaligenes*, the genus *Rhodobacter*, the genus *Ralstonia*, the genus *Acidovorax* and the like can be used. Among these, microorganisms belonging to the genus *Burkholderia* are preferable. A specific example of the microorganism belonging to the genus *Burkholderia* is *Burkholderia arboris* SL1B1 strain. The strain has been deposited to the National Institute of Technology and Evaluation, Patent Microorganisms Depository as Accession No. NITE P-724, and can be subdivided by undergoing a predetermined procedure. The strain decomposes oils and fats at a high rate. Furthermore, said strain can grow and decompose oils and fats even under a weak acidic condition.

The lipase secretion ability of the microorganism can be evaluated by measuring the lipase activity of a culture supernatant obtained by centrifuging a culture broth of the microorganism. The lipase activity can be determined by conducting an enzyme reaction using 4-nitrophenyl palmitate (4-NPP), which is an ester of palmitic acid and 4-nitrophenol, as a substrate, and measuring the amount of the 4-nitrophenol generated by the hydrolysis of the ester by measuring the absorbance at 410 nm. First, 4-NPP (18.9 mg) is added to 3% (v/v) Triton X-100 (12 ml) and dissolved at 70° C. to give a substrate solution. 1 mL of the substrate solution, 0.9 mL of ion exchange water and 1 mL of a 150 mM GTA buffer (obtained by adding NaOH or HCl to 150 mM of 3,3-dimethylglutaric acid, 150 mM of Tris and 150 mM of 2-amino-2-methyl-1,3-propanediol, and adjusting the pH to 6) are put into a cell, and kept warm at 28° C. for 5 minutes. 0.1 mL of the culture supernatant is added thereto, and the value at 410 nm is measured under stirring. The lipase activity is obtained by measuring the activity by defining the amount of the enzyme that produces 1 μmol of 4-nitrophenol as 1 unit (U), and calculating the units per 1 mL of the culture supernatant.

The ability of the microorganism to decompose triacylglycerol and fatty acids can be evaluated by quantifying fatty acids contained in triacylglycerol remaining in the culture medium and free fatty acids generated by the hydrolysis by gas chromatography. Specific procedures for the quantification are shown as follows. Firstly, 1 mL of the culture supernatant is made acidic by hydrochloric acid, and 2 mL of chloroform is added thereto. The mixture is stirred for 2 minutes and then centrifuged, and 1 mL of the chloroform layer is transferred to another container and concentrated by evaporating the solvent 2 mL of a methanolysis solution (methanol:sulfuric acid =17:3) is added, and the mixture is heated at 100° C. for 2 hours, whereby the triacylglycerol and free fatty acids are methyl-esterified. Thereafter 2 mL of chloroform and 1 mL of pure water are added, and the mixture is stirred, and the chloroform layer is analyzed by gas chromatography to quantify the methyl ester of the fatty acid.

The abilities of the microorganism to hydrolyze triacylglycerol and to consume the fatty acids can be evaluated by analyzing the triacylglycerol remaining in the culture medium and the fatty acids as hydrolyzed products thereof by thin layer chromatography (TLC). Specific procedures are shown as follows. 40 mL of ethyl acetate is added to 20 mL of the culture supernatant, and the mixture is made acidic with hydrochloric acid and stirred for 10 minutes. Thereafter 20 mL of the ethyl acetate layer is concentrated and dissolved in 4 mL of chloroform, and 2 μL is applied onto TLC and developed by a chloroform:acetone (96:4) solution. As standard substances for the triacylglycerol and a fatty acid, trioleic acid and oleic acid can be respectively used. After the development, a 4% ethanol solution of (w/v) 12 molybdo (IV) phosphoric acid is sprayed thereon, and heating is conducted at 100° C. for 30 minutes, whereby the triacylglycerol and free fatty acids are visualized.

As shown in the following Examples, as a result of the examination by the present inventors, it was proved that *Yarrowia lipolytica*, which had been identified as being excellent in ability to assimilate free fatty acids, did not secrete a lipase. Based on this fact, in one embodiment of the present invention, *Yarrowia lipolytica* having a property that it does not secrete a lipase is used. On the other hand, it was proved that *Yarrowia lipolytica* that had been successfully obtained grew symbiotically with *Burkholderia arboris* and attained effective decomposition and removal of oils and fats. Based on this fact, *Yarrowia lipolytica* that can grow symbiotically with *Burkholderia arboris* is preferably used. In addition, in this case, *Burkholderia arboris* is used in combination. Specific examples of the *Yarrowia lipolytica* that can grow symbiotically with *Burkholderia arboris* are 1A1 strain, 8A1 strain, 8D1 strain and 24B2 strain that are shown in the following Examples. Among these, 1A1 strain, which is excellent in effect of combination use with *Burkholderia arboris* SL1B1 strain, is preferable. The strain has been deposited to a predetermined authority depository shown below.

Depositary Institution: National Institute of Technology and Evaluation, Patent Microorganisms Depository (2-5-8 Kazusa Kamatari, Kisarazu-shi, Chiba 292-0818 JAPAN)

Date of Deposition: Nov. 25, 2011

Accession No.: NITE BP-1167

In a further embodiment of the present invention, a microorganism that assimilates glycerol, which is one of hydrolysis products of triacylglycerol, is used in combination to thereby prevent decrease of the oil and fat decomposition velocity due to the accumulation of glycerol. The microorganism herein is not especially limited as long as it can assimilate glycerol, and for example, eubacteria, yeasts and filamentous fungi can be used. Yeasts belonging to the genus *Candida* are preferably used. A specific example of the yeast belonging to the genus *Candida* is *Candida cylindracea* SL1B2 strain (Patent Literature 2). The strain has been deposited to the National Institute of Technology and Evaluation, Patent Microorganisms Depository as Accession No. NITE BP-00714, and can be subdivided by undergoing a predetermined procedure. The strain has an excellent ability of glycerol assimilation, and also has a property that it can grow symbiotically with *Burkholderia arboris*. Accordingly, combination use with *Candida* cylindracea SL1B2 strain is especially preferable in an embodiment in which *Burkholderia* arboris is used (namely, an embodiment in which *Burkholderia* arboris, which secretes a lipase, is used for forming a condition under which triacylglycerol is hydrolyzed into fatty acids and glycerol). A specific example of the *Burkholderia* arboris herein is the above-mentioned *Burkholderia* arboris SL1B1 strain, which has been deposited with the National Institute of Technology and Evaluation, Patent Microorganisms Depository (Accession No. NITE BP-00724).

The ability of the microorganism to decompose and consume glycerol can be evaluated by quantifying the glycerol concentration in the culture supernatant by an enzyme process. For this quantification, a commercially available quantification kit such as F kit-glycerol (manufactured by Roche) can be used. Furthermore, the abilities of the microorganism to assimilate the triacylglycerol, fatty acids and glycerol can be evaluated by investigating the growth potentials in culture media containing triacylglycerol, a fatty acid and glycerol respectively as a single carbon source. As a method for investigating the growth potential, a method including measuring the optical density of microbial cells is exemplified, but the method is not suitable in some cases since a culture broth becomes cloudy also by the emulsification of a substrate in the cases when triacylglycerol or a fatty acid is used as a carbon source. As a more versatile method, a method for measuring colony forming units (CFU) is exemplified. Aliquot of undiluted and diluted culture broth are spread onto an agar culture medium, and colonies formed by static culturing are counted.

The temperature condition in applying the method for decomposing and removing oils and fats according to the present invention is not especially limited as long as the *Yarrowia lipolytica* employed can grow and assimilate a free fatty acid. A preferable temperature is in the range from 20° C. to 40° C. The *Yarrowia lipolytica* 1A1 strain shows a fine activity also under a low temperature condition in which the decomposition efficiency of the oils and fats is decreased. Especially in the case when *Burkholderia arboris* SL1B1 strain is used in combination, the growth of the *Burkholderia arboris* SL1B1 strain is also promoted, and thus the efficiency of decomposition and removal of oils and fats is significantly increased as compared to the case when the *Burkholderia* arboris SL1B1 strain is used singly.

In the case when two or more kinds of microorganisms are used in combination, such as the case when *Yarrowia lipolytica* and *Burkholderia arboris* are used in combination, and the case when *Candida cylindracea* is further used in combination, for example, the respective microorganisms are separately prepared and subjected to use. Alternatively, a mixture (mixed microorganism agent) may be prepared in advance and used. In the case when three or more kinds of microorganisms are used in combination, it is not necessary to form all of the microorganisms into one mixed microorganism agent (for example, in the case when three kinds of microorganisms are used, a microorganism agent containing one kind of microorganism and a microorganism agent containing the other two kinds of microorganisms are prepared, and these are used in combination).

The use amount of the *Yarrowia lipolytica* used in the present invention can be preset with consideration for a subject to be treated, treatment conditions and the like. As an example of the used amount, in the case when the method is applied to factory waste water (having a normal hexane value of about 300 mg/L), a *Yarrowia lipolytica* cultured product of from $1\times10^4$ CFU/mL to $1\times10^9$ CFU/mL is added by from 1 mL to 100 mL per 1 L of the volume of the treatment tank. In the case when the method is applied to a grease trap, a *Yarrowia lipolytica* cultured product of from $1\times10^4$ CFU/mL to $1\times10^{11}$ CFU/mL is added by from 1 mL to 100 mL per 1 L of the volume of the grease trap. Similarly, the use amount of the component to be used in combination may be preset with consideration for a subject to be treated, treatment conditions and the like. The use amount in the case when *Burkholderia arboris* is used in combination is, for example, from 1 mL to 100 mL of a cultured product of from $1\times10^4$ CFU/mL to $1\times10^9$ CFU/mL per 1 L of the volume of the treatment tank (in the case of a treatment of waste water), or from 1 mL to 100 mL of a cultured product of from $1\times10^4$ CFU/mL to $1\times10^{11}$ CFU/mL per 1 L of the volume of the grease trap (in the case of clarification of a grease trap). Similarly, the use amount in the case when *Candida cylindracea* is used in combination is, for example, from 1 mL to 100 mL of a cultured product of from $1\times10^4$ CFU/mL to $1\times10^9$ CFU/mL per 1 L of the volume of the treatment tank (in the case of a treatment of waste water), or from 1 mL to 100 mL of a cultured product of from $1\times10^4$ CFU/mL to $1\times10^{11}$ CFU/mL per 1 L of the volume of the grease trap (in the case of clarification of a grease trap). In addition, in order to retain the effect, it is preferable to add or replace the microorganism at intervals of, for example, from 1 hour to 7 days. Similarly to the use amount of the microorganism, the frequency of the addition or replacement may be preset with consideration for a subject to be treated, treatment conditions and the like.

2. Microorganism and Oil and Fat Decomposing Agent Having Excellent Ability of Assimilating Free Fatty Acid The second aspect of the present invention provides a novel microorganism having excellent ability of assimilating free fatty acids, and an oil and fat decomposing agent including the microorganism as an active ingredient. As mentioned above, the *Yarrowia lipolytica* strains that had been successfully identified by the present inventors showed a property that they have an excellent ability of assimilating free fatty acids but do not secrete a lipase. Furthermore, it has been clarified that the *Yarrowia lipolytica* can grow symbiotically with *Burkholderia arboris* and can attain effective decomposition of oils and fats. Based on these findings, *Yarrowia lipolytica* having the following properties is provided: (1) the *Yarrowia lipolytica* assimilates free fatty acids; (2) the *Yarrowia lipolytica* does not secrete a lipase; and (3) the *Yarrowia lipolytica* can grow symbiotically with *Burkholderia arboris*. Since the *Yarrowia lipolytica* of the present invention has the characteristic of (3), it is suitable for combination use with *Burkholderia arboris*. Specifically, the *Yarrowia lipolytica* prevents the accumulation of free fatty acids and promotes the hydrolysis of triacylglycerol, and also promotes the growth of *Burkholderia arboris*, by combination use with *Burkholderia arboris*, whereby the decomposition of oils and fats is further promoted. A specific example of the *Yarrowia lipolytica* of the present invention is 1A1 strain specified by Accession No. NITE BP-1167.

In the oil and fat decomposing agent of the present invention, the *Yarrowia lipolytica* of the present invention is applied to hydrolyzed products of triacylglycerol. Namely, the *Yarrowia lipolytica* is used as an active ingredient. Alternatively, the *Yarrowia lipolytica* and a component that hydrolyzes triacylglycerol into fatty acids and glycerol (hereinafter referred to as "triacylglycerol hydrolysis component") are used in combination. According to the oil and fat decomposing agent of the embodiment, the decomposition of the oils and fats is conducted by the triacylglycerol hydrolysis component, whereas the accumulation of the fatty acids (free fatty acids), which are hydrolysis products of the triacylglycerol, is prevented by the *Yarrowia lipolytica*. As a result, effective decomposition and removal of oils and fats can be achieved. In the present specification, "the *Yarrowia lipolytica* and triacylglycerol hydrolysis component are used in combination" or "including the *Yarrowia lipolytica* and triacylglycerol hydrolysis component in combination" refers to that the *Yarrowia lipolytica* and triacylglycerol hydrolysis component are used in combination. Typically, the oil and fat decomposing agent of the present invention is provided as a formulated agent obtained by mixing the *Yarrowia lipolytica* of the present invention and the triacylglycerol hydrolysis component. For example, the oil and fat decomposing agent is obtained by mixing a cultured product of the *Yarrowia lipolytica* of the present invention and the triacylglycerol hydrolysis component. As the triacylglycerol hydrolysis component, lipase or a microorganism capable of secreting a lipase is used. The lipase and the microorganism capable of secreting a lipase are as explained in the first aspect of the present invention. As the microorganism capable of secreting a lipase, *Burkholderia arboris* is preferably used, and *Burkholderia arboris* SL1B1 strain specified by Accession No. NITE P-724 is further preferably used.

On the other hand, for example, the oil and fat decomposing agent of the present invention can also be provided in the form of a kit including a first element containing *Yarrowia lipolytica* and a second element containing a triacylglycerol hydrolysis component. In this case, the two elements are used simultaneously or at predetermined intervals. Preferably, the two elements are used simultaneously. The "simultaneously" as used herein does not require strict simultaneity. Accordingly, the concept of "simultaneously" herein naturally includes the case when the two elements are used under a condition without a temporal difference as in an embodiment in which the two elements are mixed, and thereafter added/administered or the like, and also includes the case when the two elements are used under a condition without a substantial temporal difference, such as the case when one element is added/administrated, and the other is then added/administrated immediately after the administration.

It is also preferable to form an oil and fat decomposing agent containing *Yarrowia lipolytica*, and use a triacylglycerol hydrolysis component in combination upon when the oil and fat decomposing agent is used. The timings of use of the oil and fat decomposing agent containing the *Yarrowia lipolytica* and use of the triacylglycerol hydrolysis component in this case are similar to those in the case of the above-mentioned form of a kit. Namely, it is preferable that the two elements are simultaneously administered, but the two elements may be used at a predetermined temporal difference. Furthermore, conversely to the above-mentioned embodiment, it is also preferable to form an oil and fat decomposing agent containing the triacylglycerol hydrolysis component, and use the *Yarrowia lipolytica* in combination when the oil and fat decomposing agent is used. In this case, the timings of use conform to those in the case of the above-mentioned embodiment.

It is preferable to incorporate a microorganism that assimilates glycerol as a third component in the oil and fat decomposing agent of the present invention. According to the embodiment, the accumulation of glycerol, which is a hydrolysis product of triacylglycerol, can be prevented, and thus an oil and fat decomposing agent that can attain further effective oil and fat decomposition is obtained. The microorganism that assimilates glycerol is as explained in the first aspect of the present invention. Meanwhile, as the microorganism that assimilates glycerol, *Candida cylindracea* is preferably used, and *Candida cylindracea* SL1B2 strain specified by Accession No. NITE P-714 is further preferably used.

A component that enhances the activity of the used microorganism (for example, a carbon source, a nitrogen source), a desiccant protective agent, a component for retaining the microorganism for a long time period, an antiseptic agent, an excipient, a reinforcing agent, an antioxidant and the like may further be incorporated.

The oil and fat decomposing agent of the present invention is provided in a state of a liquid, or a solid or a dried form. Examples of the liquid form can include a culture broth of a microorganism (this may be concentrated or diluted as necessary), a liquid form obtained by collecting a microorganism from a culture broth by centrifugation or the like, and dispersing the microorganism in water, a buffer or a culture medium or the like, and the like. With respect to the solid, a solid dehydrated by centrifugation, press compression or the like, a solid in a paste state or a mayonnaise state, which is like an intermediate between a solid and a liquid, a dried form formed by drying, and the like can be exemplified. The dried form can be obtained by, for example, subjecting grown cells to freeze-drying or drying under a reduced pressure, and examples of the specific shape thereof can include a powder, a granule and a tablet.

A microorganism that constitutes the oil and fat decomposing agent of the present invention may be immobilized. Namely, a microorganism immobilized on a support may also be used. Examples of the material for the support used for immobilizing can include carbon fibers (PAN-based, pitch-based, phenol resin-based and the like), polyethylene resins, polypropylene resins, polyurethane resins, polystyrene resins, polyvinyl chloride resins, polyvinyl acetate resins, polyvinyl alcohol resins, polyethylene glycol resins, acrylic resins, gelatin, sodium alginate, carrageenan and dextrin, and composites thereof. In order to increase the immobilization rate of the microorganism or to increase the action efficiency of the microorganism, it is preferable to use a porous material or a fibrous support. The shape of the support is not especially limited. Examples of the shape of the support are a cubic form, a cuboid form, a columnar form, spherical form, a disk form and a sheet form. For the technology for immobilizing the microorganism, for example, "Treatment of Waste Water by Microorganism Immobilization Process" (written and edited by Ryuichi Sudo, The Industrial Water Institute)", "Water Treatment by Microorganism Immobilization Process—Support Immobilization Process, Entrapping Immobilization Process, Biological Active Carbon Process (Series of New Water Treatment (1)) (written by Kazuhiro Mochizuki, Katsutoshi Hori and Hideki Tachimoto, NTS Inc.)" and the like serve as useful references.

EXAMPLES

1. Screening of Bacteria that Decompose and Assimilate Fatty Acids

In order to select microorganisms specialized for decomposition of fatty acids, 29 kinds of environment samples in total such as a grease in a grease trap tank, soil, sludge and lake water were obtained, and each sample was applied onto an agar culture medium containing oleic acid as a sole carbon source, and the formed single colony was collected and inoculated on the same culture medium; these operations were repeatedly conducted, whereby 12 strains of microorganisms that decompose and assimilate a fatty acid in total were successfully obtained. These 12 strains of microorganisms were each added to an inorganic salt liquid culture medium containing oleic acid as a sole carbon source, cultured under shaking at 28° C. for 24 hours, and compared for the growth of the microorganisms and the ability of decomposing oleic acid. Furthermore, the lipase secretion ability was evaluated by using an inorganic salt agar culture medium containing triacylglycerol for the effective evaluation of a lipase-secreting microorganism as a sole carbon source. The lipase-secreting microorganism forms a clear zone (halo) on the periphery of the colony formed on the above-mentioned agar culture medium. Therefore, a microorganism that does not form a halo does not have a lipase-secretion ability. The strains as candidates for fatty acid-decomposing microorganisms are shown in Table 1. The degree of cloudiness of the culture broth was evaluated as the growth ability, and the degree of the amount of dispersion of the oil droplets that came to the surface of the culture broth was evaluated as the ability of decomposing oleic acid, respectively, by five-grade evaluation by visual observation, and a lipase-secreting microorganism *Burkholderia arboris* was used for comparison. Furthermore, for the identification of the candidate strains, the homology was evaluated from the base sequence of 16S or 26S ribosomal RNA and described. As a result, many strains belonging to the genus *Yarrowia* or genus *Burkholderia* were selected as candidate strains. With further limitation, *Yarrowia lipolytica* (*Y. lipolytica*) was consequently preferable as a candidate. These strains do not have a lipase-secretion ability and a triacylglycerol decomposition ability, but have a high ability to decompose oleic acid and a high growth ability.

TABLE 1

| No. | Growth ability | Decomposition ability | Halo formation | Corresponding bacterial species |
|---|---|---|---|---|
| Control | 3 | 3 | + | *Burkholderia arboris* |
| 1A1 | 4 | 4 | − | *Yarrowia lipolytica* strain |
| 8A1 | 5 | 5 | − | *Yarrowia lipolytica* strain |
| 8D1 | 4 | 4 | − | *Yarrowia lipolytica* strain |
| 19B1 | 3 | 2 | + | *Burkholderia cenocepacia* strain |
| 19C1 | 3 | 2 | + | *Burkholderia cepacia* strain |
| 21A1 | 3 | 2 | − | *Burkholderia nodosa* strain |
| 22A1 | 3 | 2 | − | *Burkholderia nodosa* strain |
| 24B1 | 2 | 3 | + | *Burkholderia ambifaria* strain |
| 24B2 | 3 | 3 | − | *Yarrowia lipolytica* strain |
| 25A1 | 3 | 2 | + | *Burkholderia cepacia* strain |
| 25B1 | 3 | 2 | + | *Barkholderia cepacia* strain |
| 25C1 | 3 | 3 | + | *Burkholderia cepacia* strain |

2. Classification of 1A1 Strain

It was found by a morphological observation that 1A1 strain was a yeast, and the 1A1 strain was identified as *Y. lipolytica* based on a phylogenetic analysis based on 26S rDNA and showed 100% homology with *Y. lipolytica* NRRL YB-423 as a standard strain (FIG. 1).

3. Detailed Comparison of Abilities to Decompose Oleic Acid

The 12 strains that had been screened in advance were each subjected to preculturing for 24 hours in an inorganic salt culture medium to which 10 g/L of oleic acid had been added, the bacteria were collected and washed, the optical density OD600 of the cell suspension was adjusted to be 0.01, and the bacteria were inoculated into an inorganic salt liquid culture medium to which 2 g/L of oleic acid had been added. Cultivation was conducted at 28° C. for 48 hours by using a flask having a volume of 100 mL, and the concentration of the residual fatty acid in the culture medium was evaluated by thin layer chromatography (TLC). For the purpose of comparison, *B. arboris* SL1B1 strain, which has a high ability of triacylglycerol decomposition, was also subjected to a test. As a result, it was found that *Y. lipolytica* 1A1 strain had a very high ability of oleic acid decomposition as compared to the other strains containing *B. arboris* SL1B1 strain (FIG. 2).

4. Ability of Assimilating Free Fatty Acids and Triacylglycerol

The ability of *Y. lipolytica* 1A1 strain to grow by assimilating triacylglycerol and oleic acid was verified. The growth was observed on agar culture media to which 10 g/L (1%) of canola oil and 10 g/L (1%) of oleic acid had been respectively added as carbon sources (FIG. 3). As a bacterium for comparison, *B. arboris* SL1B1 strain was used. *B. arboris* grew on both of the culture media. On the other hand, *Y. lipolytica* 1A1 strain was able to grow on the oleic acid culture medium, but was not be able to grow on the canola oil culture medium. Accordingly, *Y. lipolytica* 1A1 strain has an ability to assimilate oleic acid, which is a hydrolysis product of triacylglycerol, but cannot secrete a lipase and thus cannot hydrolyze triacylglycerol, and thus cannot grow on triacylglycerol.

5. Oil and Fat Decomposition Experiment 1

10 g/L of canola oil was added to 3 L of an inorganic salt culture medium, and pure culturing of *B. arboris* SL1B1 strain or mix culturing of *B. arboris* SL1B1 and *Y. lipolytica* 1A1 strain was conducted at pH 6.0 and a temperature of 28° C. in a fermenter, and the decomposition behavior of the oil was analyzed. Sampling was conducted every 6 hours, and the fatty acid concentration and microorganism concentration were examined. The microorganism concentration was determined by colony counting on a LB culture medium, and the fatty acid was analyzed quantitatively by gas chromatography and qualitatively by thin layer chromatography. As a result, 10 g/L of triacylglycerol completely decomposed and disappeared within 30 hours in either of the pure culturing and mix culturing (FIG. 4). In the pure culture, the cell concentration of *B. arboris* reached $10^{10}$ cells/mL. In the mixed culture, both *B. arboris* and *Y. lipolytica* 1A1 strain reached $10^7$-$10^8$ cells/mL. According to this experiment, it was proved that these two kinds of microorganisms were capable of being mix-cultured. However, at this oil concentration and temperature, the oil and fat decomposition ability of *B. arboris* was sufficiently exerted, and the effect of mixing with *Y. lipolytica* 1A1 strain was not able to be observed.

6. Oil and Fat Decomposition Experiment 2

10 g/L of canola oil was added to 3 L of an inorganic salt culture medium, and pure culturing of *B. arboris* SL1B1 strain or mix culturing with *Y. lipolytica* 1A1 strain was conducted at pH 6.0 and a temperature of 22° C. by using a fermenter, and the decomposition behavior of the oil was analyzed. Sampling was conducted every 6 hour, and the fatty acid concentration and microorganism concentration were examined. The analysis method was similar to that of Experiment 5. As a result, it took 42 hours or more for the complete decomposition and disappearance of triacylglycerol in the pure culturing of *B. arboris*, whereas the hydrolysis velocity of the triacylglycerol and the consumption velocity of fatty acids were accelerated in the mix culturing, and triacylglycerol and fatty acids from 10 g/L of canola oil, almost decomposed and disappeared within 30 hours (FIG. 5). Furthermore, the bacterial density of *B. arboris* reached $10^8$ cells/mL in the pure culturing, and *B. arboris* and *Y. lipolytica* 1A1 strain reached $10^9$ cells/mL and $10^6$ cells/mL, respectively, in the mix culturing. At a low temperature of 22° C., the free fatty acid assimilation velocity of *B. arboris* was slow, and the free fatty acids remained even at 42 hours. By adding *Y. lipolytica* 1A1 strain, which is an oleic acid-assimilating bacterium, an effect of promoting the decomposition and assimilation of the free fatty acids was observed, and the fatty acid was not detected at all at 36 hours even by TLC.

7. Oil and Fat Decomposition Experiment 3

30 g/L of canola oil was added to 3 L of an inorganic salt culture medium, and pure culturing of *B. arboris* SL1B1 strain or mix culturing with *Y. lipolytica* 1A1 strain was conducted at pH 6.0 and a temperature of 22° C. by using a fermenter, and the decomposition behavior of the oil was analyzed. Sampling was conducted every about 12 hours, and the fatty acid concentration and microorganism concentration were examined. The analysis method was similar to that of Experiment 5. As a result, it took 144 hours for the complete disappearance of the fatty acid in the pure culturing of *B. arboris* SL1B1 strain, whereas the decomposition velocities of the triacylglycerol and fatty acids were dramatically accelerated in the mix culturing with *Y. lipolytica* 1A1 strain, and the fatty acid completely disappeared within 48 hours (FIG. 6). Furthermore, *B. arboris* reached $10^8$ cells/mL in the pure culturing, whereas both *B. arboris* and *Y. lipolytica* 1A1 strains grew with going beyond $10^8$ cells/mL in the mixed culture. Under a low temperature condition and in the presence of a large amount of oils and fats, the accumulation amount of the free fatty acid was high, and the decomposition and assimilation of the free fatty acids were significantly promoted by the coexistence of *Y. lipolytica* 1A1 strain.

8. Example Using Actual Waste Water

A microorganism formulation in which *B. arboris* SL1B1 strain and *Y. lipolytica* 1A1 strain were mixed was injected into oil-containing waste water (about 300 mg/L in terms of normal hexane value) from a certain food factory, and an oil and fat decomposition test by culturing with aeration and agitation was conducted with controlling temperature and pH to 30° C. and 7, respectively. The normal hexane values at after 12 hours and 18 hours were measured. The number of the injected viable cells (CFU) was shown as a horizontal axis in a graph, and the decreased values of the normal hexane values at after 12 hours and 18 hours were shown as a vertical axis (FIG. 7). The decreased value of the normal hexane value was higher at a larger number of the injected viable cells, and in the case when the number of the injected viable cells was $10^6$ cell/mL or more, the substance extracted with the normal hexane in the waste water almost disappeared at after 18 hours (about 300 mg/L in terms of decreased value of normal hexane value). Furthermore, the change in the number of viable cells at after 12 hours and 18 hours for each number of the injected viable cells are also shown in FIG. 8. It was confirmed that the number of viable cells increased over time. By this way, it was verified that a mixed microorganism formulation of *B. arboris* SL1B1 strain and *Y. lipolytica* 1A1 strain is also effective for the decomposition of oils and fats in actual waste water.

9. Verification Test in Grease Trap

An experiment in which a mixed microorganism formulation of two kinds: *B. arboris* SL1B1 strain and *Candida cylindracea* SL1B2 strain or a mixed microorganism formulation of three kinds: *B. arboris* SL1B1 strain, *C. cylindracea* SL1B2 strain and *Y. lipolytica* 1A1 strain was injected into a grease trap in a certain restaurant, was conducted. Since the constitution of the grease trap is similar to that of a conventionally-known one, the detailed explanation is omitted, and the outline is stated as follows. The grease trap is constituted by three tanks that are partitioned by boards, and the respective tanks are connected at the bottom parts. Waste water flows into the first tank, further flows into the second tank and third tank through the opened parts of the bottom parts, and finally flows out of the third tank. The internal capacity is 200 L, and the average retention time of the waste water is 12 minutes. In order to promote the retention of the microorganism, charcoal was placed at the bottom of the grease trap for immobilizing the microorganism onto it. The microorganism formulation was supplied at immediately after the stopping of the flow-in and flow-out of the waste water from the kitchen of the restaurant in the night, and the collection of water for the measurement of normal hexane values was conducted during the operation in the daytime. 400 mL of the microorganism formulation was injected into the first tank every night. As a result, an oil and fat decomposition effect was recognized by the addition of the mixed microorganism formulation of two kinds, but the oil and fat decomposition effect was exponentially increased by the addition of the mixed microorganism formulation of three kinds containing *Y. lipolytica* 1A1 strain, and at after 3 weeks from the initiation of the addition of the microorganism formulation, the normal hexane value was lower than 30 mg/L, which is a standard value of a normal hexane value in many local governments, and the low value was thereafter maintained (FIG. 9).

<Summary>

(1) *Y. lipolytica* 1A1 strain having a high ability to assimilate free fatty acids was successively obtained. Unlike known *Yarrowia lipolytica* strains, the 1A1 strain does not secrete a lipase. *Y. lipolytica* 8A1 strain, 8D1 strain and 24B2 strain also show a similar property.

(2) The *Y. lipolytica* 1A1 strain can grow symbiotically with *B. arboris* SL1B1 strain.

(3) Combination use of the *Y. lipolytica* 1A1 strain and *B. arboris* SL1B1 strain shows an extremely high ability of triacylglycerol decomposition, and is also suitable for the treatment of actual waste water. The effect by the combination use is especially significant under a low temperature or in the presence of a large amount of oils and fats.

(4) When *C. cylindracea* SL1B2 strain is used in combination in addition to *Y. lipolytica* 1A1 strain and *B. arboris* SL1B1 strain, the efficiency of decomposition is further increased, and the combination is also suitable for the clarification of a grease trap.

INDUSTRIAL APPLICABILITY

According to the method for decomposing and removing oils and fats of the present invention, the decrease of the hydrolysis velocity due to the accumulation of a decomposed product of oils and fats can be prevented by the action of *Yarrowia lipolytica* that assimilates free fatty acids, and thus effective decomposition and removal of oils and fats can be achieved. For example, the present invention can be applied to the treatment of oil and fat-containing waste water and the clarification of a grease trap. Furthermore, according to the present invention, it is also possible to decompose and remove free fatty acids contained in a hydrolyzed product of oils and fats, and the present invention can also be applied to the treatment of a hydrolyzed product of oils and fats.

The present invention is not limited at all by the above-mentioned embodiments for carrying out the invention and the explanation in Examples. Aspects modified in various ways are also encompassed in the present invention within a scope that does not deviate from the recitation of the claims and can be easily conceived by a person skilled in the art. All of the contents of the articles, patent publications, granted patent publications and the like that are clearly indicated in the present specification are incorporated herein by reference.

The invention claimed is:

1. A method for decomposing and removing oils and fats, comprising contacting *Yarrowia lipolytica* that assimilates free fatty acids, does not secrete a lipase, and can be grown symbiotically with *Burkholderia arboris*, with oils and fats to be treated under a condition which a microorganism capable of secreting a lipase is present and triacylglycerol is hydrolyzed into fatty acids and glycerol, wherein the microorganism is *Burkholderia arboris* and the *Yarrowia lipolytica* is a naturally occurring strain specified by Accession No. NITE BP-1167.

2. The method according to claim 1, wherein the *Burkholderia arboris* is a strain specified by Accession No. NITE BP-00724.

3. The method according to claim 1, wherein a microorganism that assimilates glycerol is used in combination.

4. The method according to claim 3, wherein the microorganism that assimilates glycerol is *Candida cylindracea*.

5. The method according to claim 4, wherein the *Candida cylindracea* is a strain specified by Accession No. NITE BP-00714.

6. The method according to claim 1, wherein the oils and fats to be treated are oils and fats in waste water or a grease trap.

7. A method for treating waste water, comprising decomposing and removing oils and fats in waste water by the method according to claim 1.

8. A method for clarifying a grease trap, comprising decomposing and removing oils and fats in a grease trap by the method according to claim 1.

* * * * *